United States Patent [19]

Nair et al.

[11] Patent Number: 5,013,829
[45] Date of Patent: May 7, 1991

[54] STABLE CONGENER OF 2',3'-DIDEOXYADENOSINE

[75] Inventors: Vasu Nair; Greg S. Buenger, both of Iowa City, Iowa

[73] Assignee: University of Iowa Research Foundation, Iowa City, Iowa

[21] Appl. No.: 343,334

[22] Filed: Apr. 26, 1989

[51] Int. Cl.$^5$ .......................................... C07H 19/173
[52] U.S. Cl. .......................................... 536/26; 536/24
[58] Field of Search ...................... 514/45, 46; 536/24, 536/26

[56] References Cited

U.S. PATENT DOCUMENTS

| | | | |
|---|---|---|---|
| 3,817,982 | 6/1974 | Verheyden et al. | 536/23 |
| 4,543,255 | 9/1985 | Shealy et al. | 514/258 |
| 4,704,357 | 11/1987 | Mitsuya et al. | 435/32 |
| 4,714,701 | 12/1987 | Beauchamp | 514/258 |
| 4,742,064 | 5/1988 | Vince | 514/258 |

FOREIGN PATENT DOCUMENTS

| | | |
|---|---|---|
| 0206497 | 12/1986 | European Pat. Off. . |
| 0216510 | 4/1987 | European Pat. Off. . |
| 0286425 | 10/1988 | European Pat. Off. . |
| 0302760 | 2/1989 | European Pat. Off. . |

8701284 3/1987 PCT Int'l Appl. .

OTHER PUBLICATIONS

Nair et al., J. Am. Chem. Soc., 111, 8502-8504 (1989).
Lee et al., Antimicrobial AGents and Chemotherapy, 33(3), 336-339 (1989).
Balzarini et al., (I), Biochem. Biophys. Res. Comm. 159(1), 61-67 (1989).
Balzarini et al., (II), Biochem. Biophys. Res. Comm. 145(1), 269-276 (1987).
Balzarini et al., (III), Biochem. Biophys. Res. Comm., 145(1), 277-283 (1987).
Balzarini et al., (IV), Chem. Abstr., 109: 278r (1988).
Pauwels et al., Chem. Abstr., 109: 31545e (1988).

*Primary Examiner*—Johnnie R. Brown
*Assistant Examiner*—L. Eric Crane
*Attorney, Agent, or Firm*—Zarley, McKee, Thomte, Voorhees & Sease

[57] ABSTRACT

The preseent invention is concerned with congeners of 2',3'-dideoxyadenosine (ddA) with modifications at the 2- and 8- positions to increase stability of the compounds from the standpoint of resistance to deamination and hydrolytic cleavage of the glycosidic bond.

5 Claims, No Drawings

STABLE CONGENER OF 2',3'-DIDEOXYADENOSINE

BACKGROUND OF THE INVENTION

Acquired Immune Deficiency Syndrome (AIDS) has become recognized as one of the most catastrophic diseases to confront humanity. The etiologic agent of this disease is a lymphotrophic retrovirus referred to as human immunodeficiency virus (HIV-1) (Science, 1988, 239, 573). Other retroviruses related to HIV-1 are also being identified. A few synthetic modified nucleosides have shown some promise in studies involving AIDS or AIDS-related complex (ARC) (*Proc. Natl. Acad. Sci. USA*, 1986, 83, 1911; *J. Med. Chem.*, 1986, 29, 1561). These include 3'-azido-3'-deoxythymidine (AZT), 2',3'-dideoxycytidine (ddC), and 2',3'-dideoxyadenosine (ddA). The antiviral activity of these compounds is associated with their ability to inhibit, in their phosphorylated triphosphate forms, a key enzyme in the virus life cycle, i.e. reverse transcriptase (*Proc. Natl. Acad. Sci. USA*, 1987, 84, 2033). According to Broder and coworkers (*Biochem. Pharmacol.*, 1987, 36, 1765), ddA is superior to ddC and AZT in terms of therapeutic index. However, the therapeutic efficacy of ddA is limited by its instability, both with respect to rapid enzymatic deamination by the ubiquitous mammalian enzyme, adenosine deaminase, and hydrolytic cleavage of the glycosidic bond. There is, therefore, a continuing need for novel congeners of ddA that continue to have antiretroviral activity against retroviruses such as the AIDS virus, but are more stable than ddA with respect to hydrolytic deamination of the 6-amino group and with respect to hydrolytic cleavage of the glycosidic linkage between the sugar and base moieties.

This invention has as its primary objective the fulfilling of the above need.

In particular, the objective of the present invention is the development of a series of congeners of the anti-AIDS compound, 2',3'-dideoxyadenosine, that involve strategic modification of the 2- and 8- positions such that they are stable and would therefore have markedly enhanced therapeutic potential.

A further objective is to provide an effective and direct route to the synthesis of functionalized congeners of the anti-AIDS compound, 2',3'-dideoxyadenosine.

A still further objective of the present invention is to provide therapeutic compositions containing the stable ddA congeners of the present invention.

The method and manner of accomplishing each of the above objectives of the invention will become apparent from the detailed description which follows.

SUMMARY OF THE INVENTION

The present invention is concerned with congeners of 2',3'-dideoxyadenosine (ddA) with modifications at the 2- and 8- positions to increase stability of the compounds from the standpoint of resistance to deamination and hydrolytic cleavage of the glycosidic bond.

DETAILED DESCRIPTION OF THE INVENTION

This invention relates to a series of synthesized congeners of the anti-AIDS compound, ddA, that involve strategic modifications at the 2- and 8- positions. These compounds are either very poor substrates or totally resistant to deamination by mammalian adenosine deaminase. With the exception of compound VIII, they are all more stable than ddA with respect to cleavage of the glycosidic bond between the carbohydrate (C-1') and base (N-9) moieties. Because of their strategic structural modifications and their stabilities, they are expected to have high therapeutic potential against the AIDS virus.

The 2- and 8- functionalized congeners of ddA may be represented by the following formula:

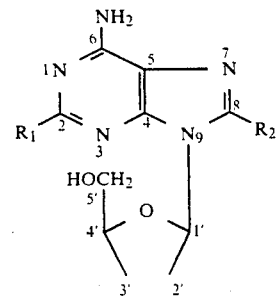

I. $R_1 = CN, R_2 = H$
II. $R_1 = CONH_2, R_2 = H$
III. $R_1 = C_2H_5, R_2 = H$
IV. $R_1 = CF_3, R_2 = H$
V. $R_1 = I, R_2 = H$
VI. $R_1 = OH, R_2 = H$
VII. $R_1 = SCH_3, R_2 = H$
VIII. $R_1 = H, R_2 = NH_2$
IX. $R_1 = H, R_2 = OCH_3$
X. $R_1 = H, R_2 = OH$
XI. $R_1 = H, R_2 = SCH_3$

In the above formula, $R_1$ and $R_2$ may be generally described as representing small functional groups such as hydrogen, hydroxy, cyanide, sulfhydryl, iodide, aminomethylene, trifluoromethyl, and $C_1$ to $C_2$ alkyl, oxyalkyl, thioalkyl, and hydroxyalkyl. While one of $R_1$ and $R_2$ may be hydrogen, both may not be hydrogen at the same time. It is most preferred that $R_2$ is hydrogen and that $R_1$ is selected from the group consisting of methyl and ethyl, trifluoromethyl, thiomethyl, hydroxy, cyano, carboxamido, methoxy, sulfhydryl, and iodo.

These compounds can be prepared using efficient and fairly straightforward syntheses, as will be apparent from the examples hereinafter described.

Generally speaking, the reactions for the formation of the 2- and 8- functionalized purine nucleosides of this invention involve new applications of a combination of chemical reactions. In particular, they include palladium-catalyzed functionalizations, deoxygenations, and photochemical functionalizations.

A common precursor to some of the compounds described is 2-iodoadenosine which can be prepared from natural guanosine in four steps as described by Nair et al. in a previous paper, J. Org. Chem., 1985, 50, 406, which is incorporated herein by reference. Palladium-catalyzed cross-coupling of 2-iodoadenosine with tri-n-butylcyanostannane in DMF resulted in regiospecific formation of 2-cyanoadenosine in 86% yield. Although 2-cyanoadenosine has been prepared previously by other workers (*Heterocycles*, 1981, 16, 1315), this represents a superior approach to this compound. Regiospecific 5'-silylation (70%) followed by treatment of the resulting silylated compound with 1,1'-thiocarbonyldiimidazole in DMF gave 2-cyano-5'-O-(t-butyldimethylsilyl)adenosine 2',3'-cyclic thiocarbonate (87%). Reductive cleavage of the latter with n-Bu₃SnH in the presence of AIBN (*J. Chem. Soc. Perkin Trans I* 1977, 1718) resulted in regiospecific 2'-deoxygenation (57% yield). This 2'-deoxygenated compound was converted to the novel 2-cyano-2',3-dideoxyadenosine (I)

through its 3'-imidazolide by treatment with n-Bu₃SnH and AIBN followed by deprotection of the silyl group with tetraethylammonium fluoride. Compound I can be easily converted to II by hydrolysis.

The key precursor for the synthesis of 2-ethyl-2',3'-dideoxyadenosine (III) was also 2-iodoadenosine. Palladiumcatalyzed cross-coupling of the latter with vinyl tri-n-butylstannane, resulted in regiospecific introduction of the vinyl group at the 2-position in almost quantitative yield. Subsequent selective 5'-silylation followed by catalytic hydrogenation of the 2-vinyl group and dideoxygenation and deprotection gave the target molecule III.

2-Trifluoromethyladenosine was the immediate precursor for the synthesis of 2',3'-dideoxy-2-trifluoromethyladenosine (IV) through the previously described dideoxygenation sequence. This precursor was prepared directly from 2-iodoadenosine in 70% yield by reaction with "CF₃Cu", an approach superior to that used previously (*J. Med. Chem.*, 1965, 8, 866) for the synthesis of 2-trifluoromethyladenosine.

A 2-halogenated congener, 2-iodo-2',3'-dideoxyadenosine, was prepared using the well known compound, 2-amino-6-chloropurine ribonucleoside, as the starting material. Dideoxygenation of this precursor using the aforementioned sequence of reactions followed by halogen amino group interchange by our previously published procedure (J. Org. Chem. 1985, 50, 406) and finally deprotection gave the novel dideoxynucleoside (V). Compound V can be converted by photochemical hydration to 2',3'-dideoxyisoguanosine (VI) in another procedure previously described by us (J. Org. Chem. 1985, 50, 406).

The precursor for the synthesis of 2',3'-dideoxy-2-thiomethyladenosine (VII) was 2-thiomethyl-adenosine which was prepared from 2-iodoadenosine by a photochemical alkylthiolation previously developed by Nair and coworkers (Synthesis, 1986, 450). Application of the dideoxygenation procedure to this precursor gave VII.

The starting compound for the synthesis of VIII was 8-bromo-2'-deoxyadenosine which was prepared by bromination of the corresponding deoxynucleoside. This starting compound was first converted to its azido derivative and then subjected to the deoxygenation procedure. During the nBu₃SnH/AIBN step, reduction of the azido group occurred concomitantly with the deoxygenation. In a related procedure, 8-bromo-2'-deoxyadenosine was converted to the corresponding 8-methoxy compound and then deoxygenated to 2',3'-dideoxy-8-methoxyadenosine (IX). 2',3'-Dideoxy-8-thiomethyl-adenoxine (XI) can be similarly prepared from 8-thiomethyl-2'-deoxyadenosine. Compound IX can be demethylated to give 2',3'-dideoxy-8-hydroxyadenosine (X).

Another aspect of the invention provides pharmaceutical compositions comprising one of the therapeutically active antiviral agents of the present invention or a pharmaceutically acceptable salt thereof, together with a pharmaceutically acceptable carrier therefor. In a particular aspect pharmaceutical compositions comprise a compound of the present invention in an effective unit dosage form.

As used herein the term "effective unit dosage" or "effective unit dose" is denoted to mean a predetermined antiviral amount sufficient to be effective against the viral organism in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg, or mammal body weight, and are used in man in a unit dosage form, administered a few times daily in the amount of 1 to 250 mg per unit dose.

For oral administration, fine powders or granules may contain diluting, dispersing and/or surface active agents, and may be presented in a draught, in water or in a syrup; in capsules or sacnets in the dry state or in a non-aqueous solution or suspension, wherein suspended agents may be included; in tablets, wherein binders and lubricants may be included; or in a suspension in water or a syrup. Where desirable or necessary, flavoring, preserving suspending, thickening or emulsifying agents may be included. Tablets and granules are preferred and these may be coated.

For parenteral administration or for administration as drops, the compounds may be presented in an aqueous solution in a concentration from about 0.1% to about 7%, most preferably from about 0.2% on a weight/volume basis. This solution may contain antioxidants, buffers, etc.

In the examples reported below the reported melting points are uncorrected and were determined on a Thomas-Hoover melting point apparatus fitted with a microscope. Nuclear magnetic resonance spectra were recorded on JEOL Model FX90Q and Bruker Model WM360 pulse Fourier transform spectrometers. Mass spectra were determined on a Hewlett-Packard 5985 GC/MS system or a VG Analytical Model ZAB-HF instrument with highresolution FAB capability. Ultraviolet spectra were recorded on a Varian Cary Model 219 or a Gilford Response spectrophotometer. Infrared spectra were recorded on an IBM Model 98 Fourier transform instrument. Lyophilizations were performed with a Virtis freezemobile 3 unit. Preparative layer chromatography plates were prepared by coating six 20 cm×20 cm plates with a slurry made from 150 g of E. Merck PF₂₅₄ silica gel in 400 mL of water. The silica gel plates were allowed to dry slowly and were then activated for 3 h at 135° C. Flash chromatography was carried out using glass columns packed with 230–400 mesh silica gel. High performance liquid chromatography was done using Altex columns packed with Amerlite XAD-4 resin (Rohm and Haas) which was ground and sieved to 40-60 um. Samples were injected with a gas tight syringe through an Altex 4-way slide valve. Separations were carried out at 20–80 psi using an FMI RRPSY-SS ¼ inch piston pump. Fractions were monitored by a Pharmacia VU-2 ultraviolet monitor and products were collected on a Gilson FC-100 fraction collector.

In the examples, the following procedures (A to F) were used.

Procedure A. Preparation of 5'-O-(tert-butyldimethylsilyl) nucleosides. A mixture of the nucleoside (2 mmol); t,-butyl-dimethylsilyl chloride (2.2 mmol), triethylamine (2 mmol), and N,N-dimethylaminopyridine (0.3 mmol) in dimethylformamide (10 ml) and dichloromethane (5 ml) was stirred at room temperature under nitrogen for 20 h. The solvents were evaporated and the residue was chromatographed on silica gel using 5% methanol/chloroform.

Procedure B. Preparation of 2',3'-O-(cyclic thiocarbonate). To a solution of the 5'-silylated nucleoside (3 mmol) in dry dimethylformamide (30 ml) was added, 1,1'-thiocarbonyldiimidazole (5.25 mmol), and the resulting mixture was stirred under nitrogen for 24 h. The solvent was evaporated and the residue was dissolved in dichloromethane (50 ml) and extracted with water (3×20 ml). The organic layer was dried ($Na_2SO_4$) and evaporated. The residue was purified by flash chromatography on silica gel using chloroform.

Procedure C. Deoxygenation of 2',3'-O-(cyclic thiocarbonate). A nitrogen-purged solution of tri-n-butyltin hydride (10.4 mmol) and azoisobutyronitrile (AIBN) (1.8 mmol) in anhydrous toluene (30 ml) was added dropwise to a refluxing solution of the cyclic thiocarbonate (2.6 mmol) in toluene (60 ml). The mixture was heated to 110° C. for 4 h, and the solvent evaporated. The residue was purified on silica gel with chloroform followed by 5% methanol/chloroform.

Procedure D. Preparation of 2'-deoxy-3'-O-(1-imidazolylthiocarbonyl)-5'-O-(t-butyldimethylsilyl) nucleosides. To a solution of the 2'-deoxynucleoside (3 mmol) in dry dimethylformamide (25 ml) was added 1,1'-thiocarbonyldiimidazole (4.5 mmol), and the mixture was stirred at 90° C. for 4 h with protection from moisture. The solvent was removed under reduced pressure and the residue was purified on silica gel using 5% methanol/chloroform.

Procedure E. Deoxygenation of 3'-O-(1-imidazolylthiocarbonyl)nucleosides. To a refluxing solution of the 3'-O-(imidazolylthiocarbonyl)nucleoside (1 mmol) in dry toluene (25 ml) was added a solution of tri-n-butyltin hydride (3.5 mmol) and AIBN (0.8 mmol) in toluene (25 ml). The mixture was refluxed for 2 h, the solvent was evaporated, and the residue was purified by preparative TLC using 10% methanol/chloroform as the eluting solvent.

Procedure F. Desilylation. The 5'-silylated-2',3'-dideoxynucleoside (1.5 mmol) was dissolved in acetonitrile (40 ml). Tetraethylammonium fluoride (4.5 mmol) was added, and the mixture was stirred at room temperature for 2 h. Water (10 ml) was added and stirring continued for 20 min. The solvents were evaporated and the residue was purified by preparative TLC (10% methanol/chloroform) to provide the dideoxynucleoside.

EXAMPLE 1

2-Cyano-2'-3'-dideoxyadenosine

I

To a solution of 2-iodoadenosine (0.500 g, 1.27 mmol) in DMF (70 mL) was added tetrakis(triphenylphosphine)palladium (0) (0.220 g, 0.19 mmol) and n-tributyltin cyanide (0.442 g, 1.39 mmol). The mixture was stirred at 120° C. for 20 h under nitrogen. The solvent was then evaporated and the residue was purified on silica gel to give 2-cyanoadenosine in 86% yield. 2-Cyanoadenosine was converted to I by using in sequence the following procedures: Procedure A (60% yield), Procedure B (89% yield), Procedure C (60% yield), Procedure D (63% yield), Procedure E (70% yield) and Procedure F (70% yield): mp 195°–197° C.; $^{13}$C NMR ($Me_2SO$-$d_6$) 625.4, 32.0, 62.6, 82.3, 84.7, 117.0, 120.7, 136.6, 141.5, 147.9, 156.2; $^1$H NMR ($Me_2SO$-$d_6$) δ2.06 (m, 2H), 2.39 (m, 2H), 3.56 (m, 2H), 4.13 (m, 1H), 4.92 (m, 1H), 6.24 (m, 1H), 7.90 (br.s, 2H), 8.59 (s, 1H); UV ($H_2O$) $\lambda_{max}$ 297 nm (ε6470), 266 nm (ε9980), 260 nm (ε9270); FAB HRMS obsd (M+ +H) 261.1069, calcd for $C_{11}H_{12}N_6O_2$ 261.1099.

EXAMPLE 2

2',3'-Dideoxy-2-ethyladenosine

III

To a solution of 2-iodoadenosine (1.585 g, 4.03 mmol) and bis(acetonitrile)palladium chloride (0.053 g, 0.20 mmol) in DMF (20 ml) was added vinyltributyltin (1.24 ml, 4.23 mmol), and the mixture stirred at 100° C. for 1 h. The reaction mixture was cooled and filtered. The solvent was evaporated and the residue was purified through silica gel with chloroform and 10% methanol/chloroform to give 1.099 g (92%) of 2-vinyladenosine: $^1$H NMR ($Me_2SO$-$d_6$) δ3.66 (m, 2H), 3.98 (m, 1H), 4.16 (m, 1H), 4.65 (m, 1H), 5.18 (d, 1H), 5.38–5.62 (m, 3H), 5.89 (d, 1H), 6.41 (dd, 1H), 6.59 (dd, 1H), 7.27 (br.s, 2H), 8.32 (s, 1H); UV (EtOH) $\lambda_{max}$ 293 nm, 271 nm, 265 nm.

2-Vinyladenosine was silylated using Procedure A (54% yield). To a solution of 5'-silylated-2-vinyladenosine (0.925 g, 2.27 mmol) in absolute ethanol (110 ml) was added 5% palladium/charcoal (0.220 g). This mixture was shaken under 33 psi of hydrogen for 2 h, and was filtered through cotton. The solvent was evaporated and the residue was purified on silica gel (5% methanol/chloroform) to give 0.670 g (72%) of 2-ethyl5'-O-(t-butyldimethylsilyl)adenosine: $^1$H NMR ($Me_2SO$-$d_6$) δ0.04 (s, 6H), 0.87 (s, 9H), 1.23 (t, 3H, J=7.3 Hz), 2.67 (q, 2H, J=7.3 Hz), 3.80 (m, 3H), 4.17 (m, 1H), 4.60 (m, 1H), 5.40 (br.s, 2H), 5.88 (d, 1H, J=5.4 Hz), 7.11 (br.s, 2H), 8.18 (s, 1H); UV (EtOH) $\lambda_{max}$ 262 nm.

2-Ethyl-5'-O-(t-butyldimethylsilyl)adenosine was dideoxygenated using in sequence Procedure B (82% yield), Procedure C (53% yield), Procedure D (76%), and Procedure E (80%) to give 2',3-dideoxy-2-ethyl-5'-O-(t-butyldimethylsilyl) adenosine. Deprotection of the latter compound by Procedure F provided III in 79% yield: mp 205°–207° C.; $^{13}$C NMR ($Me_2SO$-$d_6$) δ13.2, 26.0, 31.6, 31.9, 63.3, 81.5, 84.5, 117.5, 138.8, 149.6, 155.8, 165.4; $^1$H NMR ($Me_2SO$-$d_6$) δ1.23 (t, 3H, J=7.3 Hz), (m, 2H), 2.38 (m, 2H), 2.66 (q, 2H, J=7.3 Hz), 3.51 (m, 2H), 4.11 (m, 1H), 5.11 (m, 1H), 6.19 (t, 1H, J=5.41 Hz), 7.08 (br.s, 2H), 8.33 (s, 1H); UV ($H_2O$) $\lambda_{max}$ 262.5 nm (ε12630); FAB HRMS obsd (M+ +H) 264.1482, calcd for $C_{12}H_{17}N_5O_2$ 264.1461.

EXAMPLE 3

2',3'-Dideoxy-2-trifluoromethyladenosine

IV

A solution of trifluoromethylzinc bromide (1.308 g, 6.10 mmol) in DMF (25 mL) and HMPA (10 mL) was added to copper bromide (0.438 g, 3.05 mmol) and the resulting mixture was stirred for 30 min. 2-Iodoadenosine (0.800 g, 2.03 mmol) was added and the solution was warmed at 70° C. for 4 h. The solvents were evaporated and the residue was purified on silica gel with 10% methanol/chloroform to give 2-trifluoromethyladenosine in 63% yield. 2-Trifluoromethyladenosine was converted to IV by using in sequence the following procedures: Procedure A (58% yield), Procedure B (84% yield), Procedure C (51% yield), Procedure D (73% yield), Procedure E (75% yield), and Procedure F (53% yield): mp 173°–175° C.; $^{13}$NMR (Me$_2$SO-d$_6$) δ25.7, 31.8, 62.8, 82.1, 84.5, 119.8, 141.1, 148.3, 156.2; $^1$H NMR (Me$_2$SO-d$_6$) δ2.10 (m, 2H), 2.40 (m, 2H), 3.51 (m, 2H), 4.13 (m, 1H), 4.88 (m, 1H), 6.25 (m, 1H), 7.85 (br.s, 2H), 8.54 (s, 1H); UV (H$_2$O) λ$_{max}$ 259.5 nm (λ11300); FAB HRMS obsd (M$^+$+H) 304.0996, calcd for C$_{11}$H$_{12}$F$_3$N$_5$O$_2$ 304.1021.

EXAMPLE 4

2′,3′-Dideoxy-2-iodoadenosine

V

2-Amino-6-chloronebularine was converted to 2-amino-6-chloro-2′,3′-dideoxy-5′-O-t-butyldimethylsilyl)nebularine by using in sequence Procedures A (82%), B (73%), C (62%), D (75%), and E (83%): $^1$H NMR (Me$_2$SO-d$_6$) δ0.00 (s, 6H), 0.84 (s, 9H), 2.07 (m, 2H), 2.35 (M, 2H), 3.74(m, 2H), 4.13 (m, 1H), 6.11 (m, 1H), 6.88 (br.s, 2H), 8.27 (s, 1H), UV (EtOH) λ$_{max}$ 310 nm, 247 nm, 222 nm.

Disilylation of 2-amino-6-chloro-2′,3′-dideoxy-5′-O-(t-butyldimethylsilyl)nebularine by Procedure F gave 2-amino-6-chloro-2′,3′-dideoxynebularine in 69% yield: mp 139°–141° C.; $^1$H NMR (Me$_2$SO-d$_6$) δ2.05 (m, 2H), 2.38 (m, 2H), 3.55 (m, 2H), 4.10 (m, 1H), 4.91 (m, 1H), 6.10 (t, 1H, J=4.9 Hz), 6.88 (br.s, 2H), 8.36 (s, 1H); UV (H$_2$O) λ$_{max}$ 307 nm, 248 nm.

To a nitrogen-purged solution of 2-amino-6-chloro-2′,3′-dideoxy-5′-O-(t-butyldimethylsilyl)nebularine (0.232 g, 0.604 mmol) and diiodomethane (0.20 ml, 2.483 mmol) in hexane (50 ml) was added t-butylnitrite (0.32 ml, 2.690 mmol). The reaction mixture was stirred at 70° C. for 3 h under N$_2$. The solvents were evaporated and the residue was purified on silica gel with 5% methanol/chloroform to provide 0.087 g (29%) of 6-chloro-2-iodo-2′,3′-dideoxy-5′-O-(t-butyldimethylsilyl)-nebularine: $^1$H NMR (Me$_2$SO-d$_6$) δ-0.03 (s, 6H), 0.81 (s, 9H), 2.10 (m, 2H), 2.40 (m, 2H), 3.75 (m, 2H), 4.13 (m, 1H), 6.30 (m, 1H), 8.74 (s, 1H); UV (EtOH) λ$_{max}$ 281 nm, 255 nm, 220 nm. This 6-chloro-2-iodo compound (0.087 g, 0.175 mmol) was dissolved in 50 ml of absolute ethanol saturated with ammonia. This solution was allowed to stand at room temperature for 7 h. The solvent was allowed to stand at room temperature for 7 h. The solvent was evaporated and the residue purified on silica gel using 5% methanol/chloroform to give 0.043 g (52%) of 2-iodo-2′,3′-dideoxy-5′-O-(t-butyldimethylsilyl)adenosine which was desilylated using Procedure F to give 2-iodo-2′,3′-dideoxyadenosine (V) in 83% yield: mp dec.>220° C.; $^1$H NMR (Me$_2$SO-d$_6$) δ2.07 (m, 2H), 2.36 (m, 2H), 3.55 (m, 2H), 4.10 (m, 1H), 4.89 (m, 1H), 6.14 (m, 1H), 7.63 (br.s, 2H), 8.28 (s, b 1H); UV (H$_2$O) λ$_{max}$ 266.5 nm (λ13250); FAB HRMS obsd (M$^+$+H) 362.0088, calcd for C$_{10}$H$_{12}$IN$_5$O$_2$ 362.0114.

EXAMPLE 5

2′,3′-Dideoxy-2-methylmercaptoadenosine

VII

2-Methylmercaptoadenosine was converted to VII by using in sequence Procedures A (70% yield), B (75% yield), C (59% yield), and D, E, F (49% overall yield): mp 200°–203° C.; $^{13}$C NMR (Me$_2$SO-d$_6$) δ13.7, 26.0, 31.5, 63.1, 81.0, 84.2, 116.8, 138.2, 149.7, 155.4, 164.0; $^1$H NMR (Me$_2$SO-d$_6$) δ2.10 (m, 2H), 2.48 (m, 5H), 3.55 (m, 2H), 4.17 (m, 1H), 4.88 (t, 1H, J=5.4 Hz), 6.18 (m, 1H), 7.28 (br.s, 2H), 8.21 (s, 1H); UV (H$_2$O) λ$_{max}$ 274.5 nm (ε13150); FAB HRMS obsd (M$^+$+H) 282.1003, calcd for C$_{11}$H$_{15}$N$_5$O$_2$S 282.1025.

EXAMPLE 6

8-Amino-2′,3′-dideoxyadenosine

VIII

To a solution of 8-bromo-2′-deoxyadenosine (0.403 g, 1.22 mmol) in DMF (25 ml) was added sodium azide (0.278 g, 4.27 mmol), and the mixture stirred at 90° C. for 2 h. The solvent was removed and the residue was purified on silica gel (10% methanol/chloroform) to give 0.325 g (91%) of 8-azido-2′-deoxyadenosine: $^1$H NMR (Me$_2$SO-d$_6$)δ2.17 (m, 2H), 3.59 (m, 2H), 3.82 (m, 1H), 4.42 (m, 1H), 5.25 (m, 2H), 6.11 (m, 1H), 7.24 (br.s, 2H), 8.07 (s, 1H); UV (H$_2$O) λ$_{max}$282.5 nm; FTIF (KBr) 2155 cm$^{-1}$. 8-Azido-2′-deoxyadenosine was silylated by Procedure A (77% yield) and then reduced, dideoxygenated, and converted to 8-amino-2′,3′-dideoxyadenosine (VIII) using in sequence Procedure D (79%), Procedure E (77%), and Procedure F (81%): mp 177°–179° C., $^{13}$C NMR (Me$_2$SO-d$_6$) δ26.0, 29.0, 63.1, 79.5, 83.9, 117.1, 148.4, 148.9, 151.4, 152.3; $^1$H NMR (Me$_2$SO-d$_6$) 2.16 (m, 4H), 3.61 (m, 2H), 4.11 (m, 1H), 5.54 (m, 1H), 6.10 (m, 1H), 6.40 (br.s, 2H), 6.52 (br.s, 2H), 7.89 (s, 1H); UV (H$_2$O) λ$_{max}$273.5 nm (λ13950); FAB HRMS obsd (M$^+$+H) 251.1266, calcd for C$_{10}$H$_{14}$N$_6$O$_2$ 251.1257.

EXAMPLE 7

2′,3′-Dideoxy-8-methoxyadenosine

IX

To a solution of 8-bromo-2′-deoxyadenosine (1.85 g, 5.61 mmol) in methanol (100 ml) was added sodium methoxide (0.908 g, 16.8 mmol), and the mixture was refluxed for 20 h. The solvent was evaporated and the residue chromatographed on silica gel (5% methanol/chloroform) to give 0.865 g (55%) of 2′-deoxy-8-methoxyadenosine: $^1$H NMR (Me$_2$SO-d$_6$) δ2.11 (m, 2H), 3.53 (m, 2H), 3.81 (m, 1H), 4.10 (s, 3H), 4.38 (m, 1H), 5.24 (m, 2H), 6.18 (t, 1H, J=6.8 Hz), 6.89 (br.s, 2H), 8.02 (s, 1H); UV (H$_2$O) λ$_{max}$ 261 nm. 2′Deoxy-8-methoxyadenosine was converted to 2′,3′-dideoxy-8-methoxydenosine (IX) by using in sequence Procedures A (64%), D (83%), and E and F (79%): mp 197°–799° C.; $^{13}$C NMR (Me$_2$SO-d$_6$) δ27.0, 28.9, 57.2, 64.0, 81.1, 83.3, 114.8, 148.8, 150.7, 153.9, 154.3; $^1$H NMR (Me$_2$SO-d$_6$) δ2.16 (m, 4H), 3.51 (m, 2H), 4.10 (br.s, 4H), 5.01 (m, 1H), 6.08 (m, 1H), 6.85 (br.s, 2H), 8.03 (s, 1H); UV (H$_2$O) λ$_{max}$ 260 nm (ε11040); FAB HRMS obsd (M$^+$+H) 266.1273, calcd for C$_{11}$H$_{15}$N$_5$O$_3$ 266.1253.

What is claimed is:

1. A stable congener of 2′,3′-dideoxyadenosine of the formula:

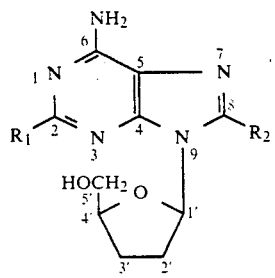

wherein $R_1$ is H and $R_2$ is OH.

2. A pharmaceutical composition which comprises an effective nontoxic antiviral treating effective amount of an 8-position modified 2′,3′-dideoxyadenosine of the formula:

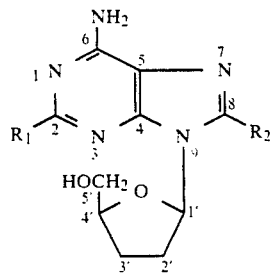

wherein $R_1$ is H and $R_2$ is OH; and a nontoxic pharmaceutically acceptable carrier for said modified 2′,3′dideoxyadenosine.

3. The pharmaceutical composition of claim 2 which is in the form of an ointment or cream.

4. The pharmaceutical composition of claim 2 which is in the form of a tablet.

5. The pharmaceutical composition of claim 2 wherein the dosage amount is from about 1 to about 250 mg per unit dose.

* * * * *

UNITED STATES PATENT AND TRADEMARK OFFICE
CERTIFICATE OF CORRECTION

PATENT NO. : 5,013,829
DATED : May 7, 1991
INVENTOR(S) : Vasu Nair, et al

It is certified that error appears in the above-indentified patent and that said Letters Patent is hereby corrected as shown below:

Column 1, line 4, add the following:

GRANT REFERENCE

Work for this invention was funded in part by a grant from the United States Army, grant number DAMD17-86-C-6001. The Government may have certain rights in this invention.

Signed and Sealed this

Twenty-fifth Day of April, 1995

Attest:

BRUCE LEHMAN

Attesting Officer        Commissioner of Patents and Trademarks